United States Patent [19]

Spademan

[11] Patent Number: 4,856,500

[45] Date of Patent: * Aug. 15, 1989

[54] CUFF DEVICE

[76] Inventor: Richard G. Spademan, 200 P St., Sacramento, Calif. 95814

[ * ] Notice: The portion of the term of this patent subsequent to Mar. 17, 2004 has been disclaimed.

[21] Appl. No.: 168,702

[22] Filed: Mar. 16, 1988

[51] Int. Cl.⁴ .......................... A61F 5/04; A61F 2/78; A61F 5/01

[52] U.S. Cl. .................................... 128/80 C; 128/88; 128/80 F

[58] Field of Search ................. 128/80 C, 80 F, 80 G, 128/88

[56] References Cited

U.S. PATENT DOCUMENTS

| | | | |
|---|---|---|---|
| 1,601,659 | 9/1926 | Van Harlingen | 128/80 C |
| 2,195,024 | 3/1940 | Bullock | 128/88 |
| 2,558,986 | 7/1951 | Seelert | 128/88 F |
| 4,220,148 | 9/1980 | Lehneis | 128/80 C |
| 4,340,041 | 7/1982 | Frank | 128/88 |
| 4,361,142 | 11/1982 | Lewis et al. | 128/88 |
| 4,506,661 | 3/1985 | Foster | 128/88 |
| 4,649,906 | 3/1987 | Spademan | 128/88 |

Primary Examiner—Edgar S. Burr
Assistant Examiner—Tonya Lamb
Attorney, Agent, or Firm—Townsend and Townsend

[57] ABSTRACT

A dynamic support (1, 40) is disclosed in which there is provided fitting system (2, 3) for engaging body parts articulated to each other, arms (4, 5) attached to and extending form the fitting system and movable attached to each other remote from the fitting system, and tightening cables (14, 71, 21, 6, 25) attached to the fitting system and arms for dynamically and temporarily tightening the fitting system differentially and progressively on the body parts in response to movement of one body part relative to the other body part.

38 Claims, 4 Drawing Sheets

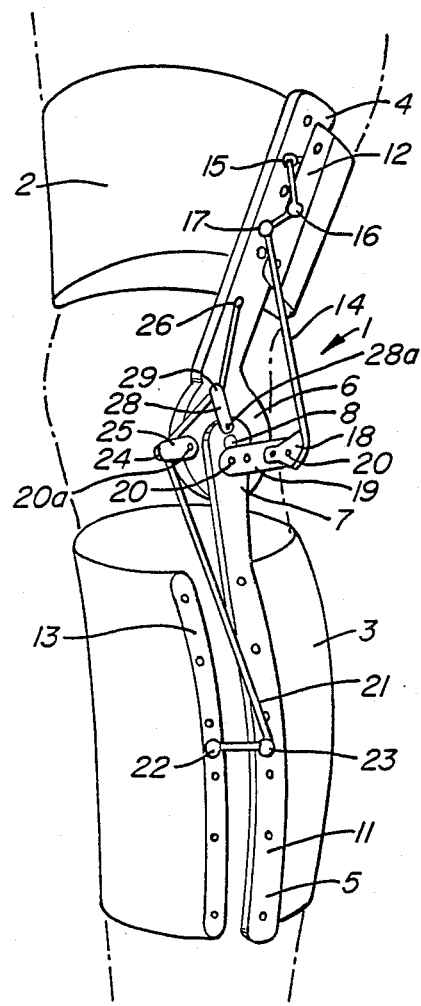
FIG._1.
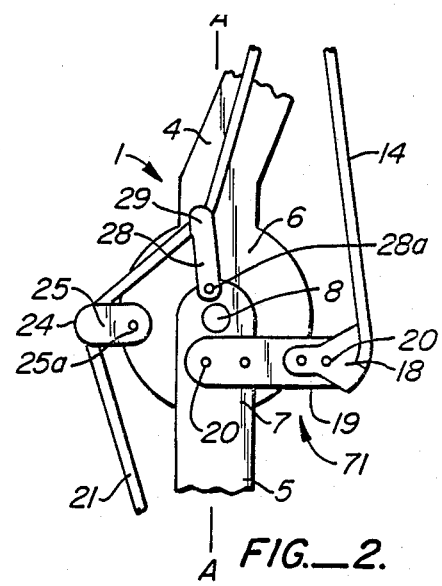
FIG._2.
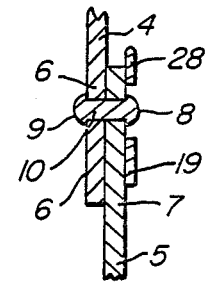
FIG._3.
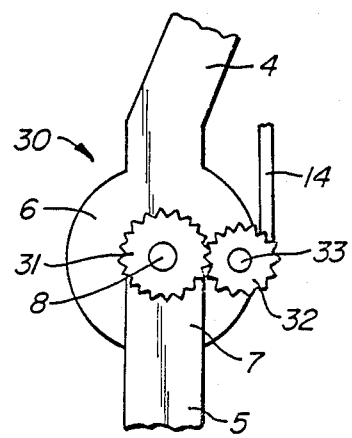
FIG._4.

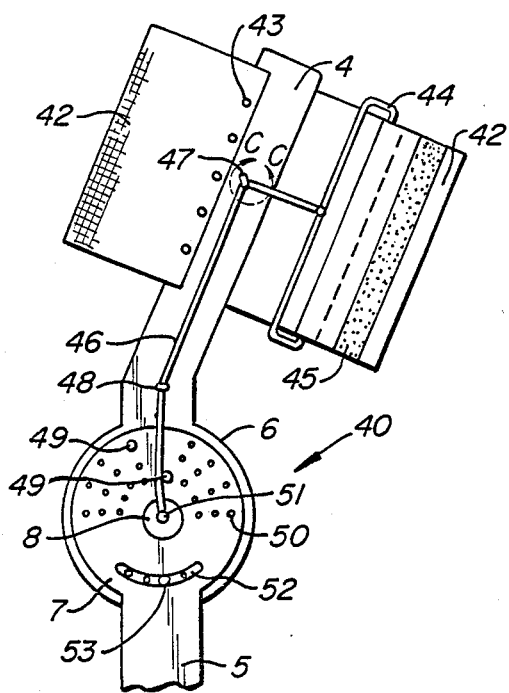
FIG._5.
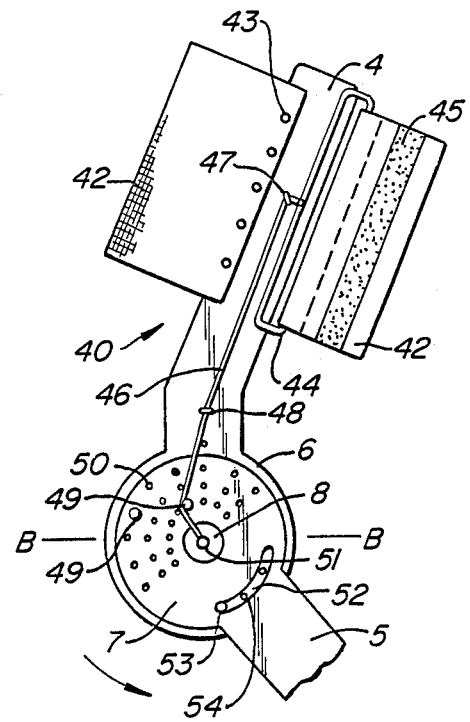
FIG._6.
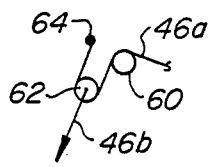
FIG._7.
FIG._8.

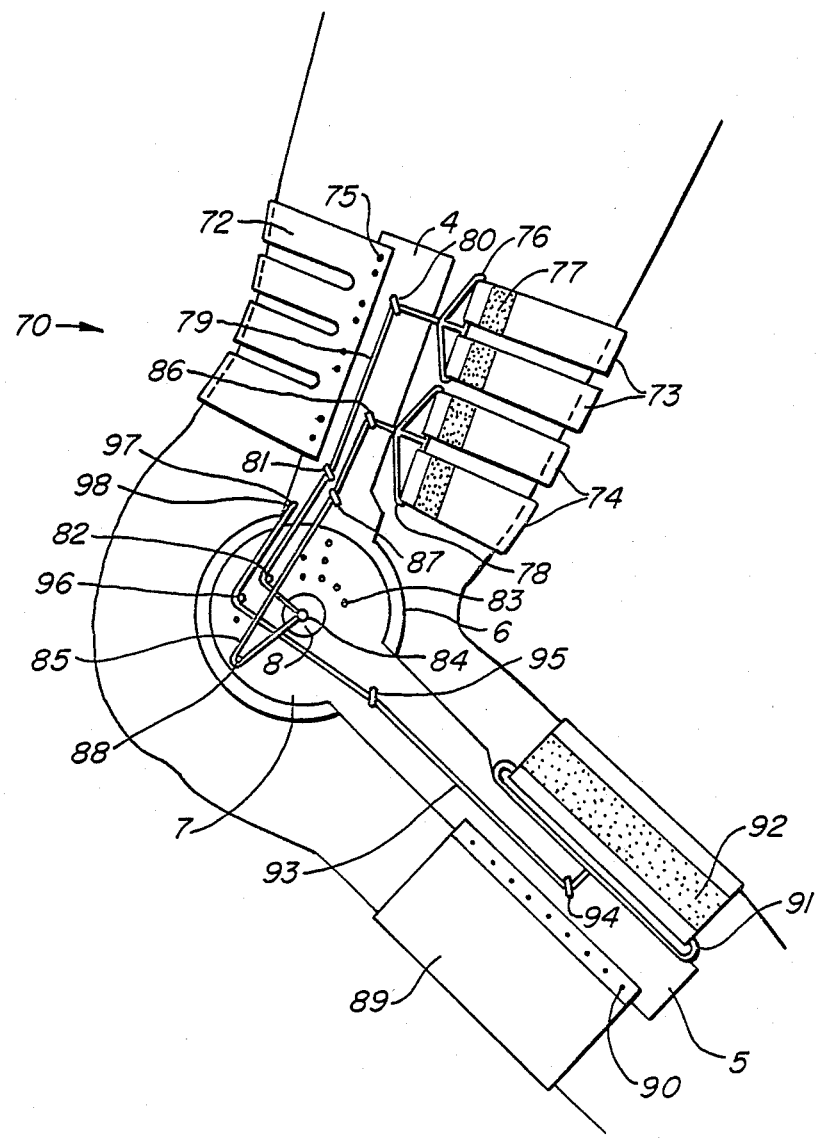
FIG._9.

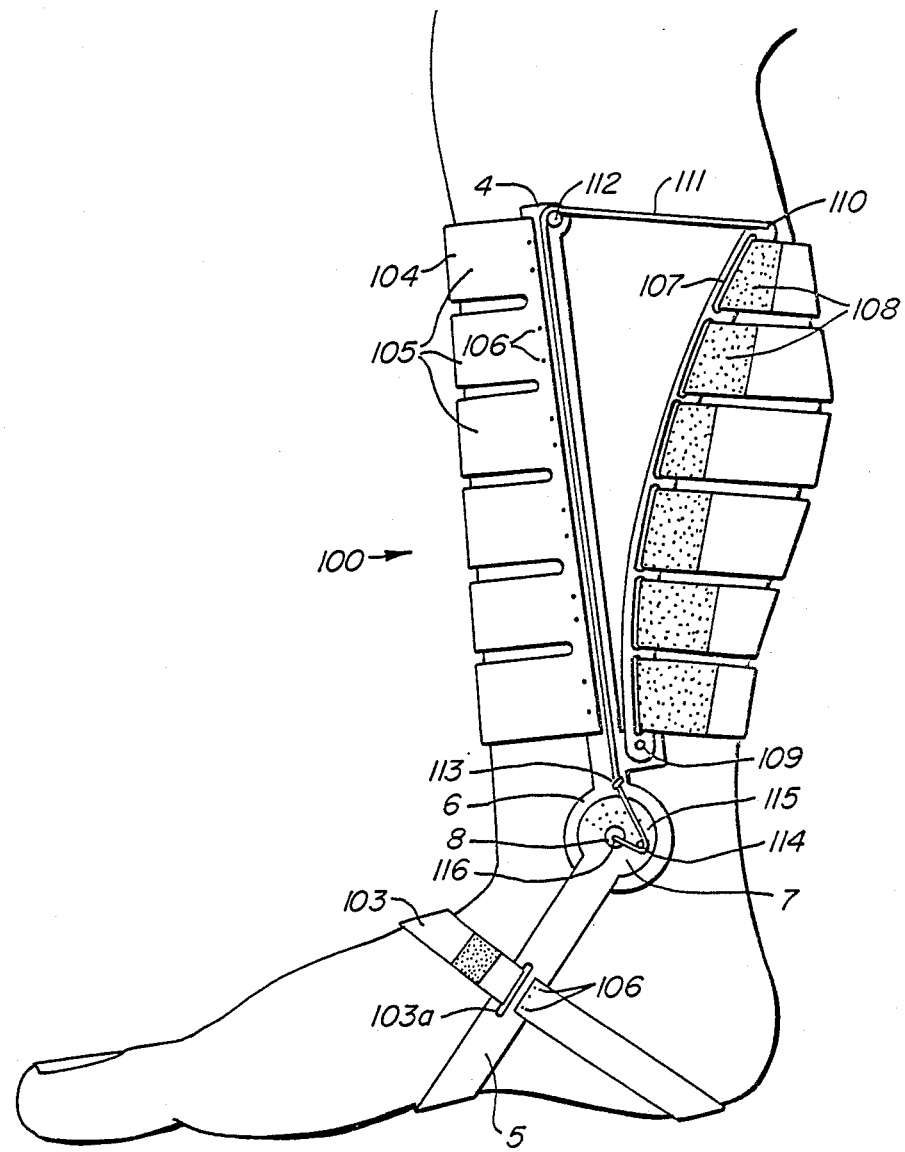
FIG._10.

4,856,500

CUFF DEVICE

BACKGROUND OF THE INVENTION

The present invention relates to therapeutic and prophylactic devices, particularly to a cuff device or dynamic support that temporarily tightens and loosens on a wearer's body part as another body part is moved.

Various compressive cuff devices are known such as the straps that hold braces on a patient's body part and trunk to protect ligaments, tendons and bones as they heal following injury or surgery. Various strapping devices are also used to help prevent injury or provide support for the chronic instability of a body part. Elastic stockings and inflatable cuffs are used to reduce edema and blood stasis in the extremities that result from disease, injury, prolonged confinement or surgery.

Unfortunately, at the present time, ideal conditions for the efficient application of these braces, cuffs and stockings cannot be achieved with conventional means. These supporting structures tend to be either too loose on the body part, in which case the support members cannot adequately stabilize the body part against undesirable or abnormal movement or fluid stasis or, more frequently, these supporting structures are held too tightly, intensifying discomfort, prolonging immobility and aggravating the problem of stasis or atrophy.

SUMMARY OF THE INVENTION

It is accordingly a primary object of the present invention to provide a cuff device or dynamic support that overcomes the drawbacks of previously known devices of the above known type.

Another object of the present invention is to provide a dynamic support that momentarily tightens on a body part in response to movement of another body part.

It is still another object of the present invention to provide a dynamic support that temporarily tightens and loosens from a close fit or snug fit position on a body part in desirable directions but not in other directions.

It is still another object of the present invention to provide a dynamic support that can be adjusted to control the rate and amount of tightening and loosening of the dynamic support on a body part in response to a predetermined movement in a predetermined direction from a predetermined position of another body part.

It is still another object of the present invention to provide a dynamic support that can temporarily differentially and progressively tighten and loosen from a close fit or snug position on a body part in response to a predetermined movement in a predetermined direction from a predetermined position of another body part.

BRIEF DESCRIPTION OF THE DRAWINGS

In the drawings:

FIG. 1 is a perspective view of a dynamic support or dynamic support of the present invention in the resting position showing various parts.

FIG. 2 is an enlarged fragmentary side elevation view of the dynamic support showing the pivot, lever and cam assembly.

FIG. 3 is a vertical sectional view taken along line A—A of FIG. 2.

FIG. 4 is an enlarged fragmentary side elevation view of the dynamic support of an alternative embodiment of the present invention showing the pivot and gear assembly.

FIG. 5 is an enlarged fragmentary side elevation view of the dynamic support of another alternative embodiment of the present invention showing the pivot and plate assembly in the resting position.

FIG. 6 is an enlarged fragmentary side elevation view of the dynamic support of FIG. 5 pivoted from the resting position.

FIG. 7 is a vertical sectional view taken along line B—B of FIG. 6.

FIG. 8 is an enlarged view of an alternative embodiment of the portion of the dynamic support of FIG. 5 identified by line C—C.

FIG. 9 is a side elevation view of the dynamic support of an alternative embodiment of the present invention showing the pivot and plate and multiple cable assembly pivoted from the resting position.

FIG. 10 is a side elevation view of the dynamic support of still another alternative embodiment of the present invention showing the pivot and plate and slotted bar in the resting position.

DESCRIPTION OF THE PREFERRED EMBODIMENTS

Referring to FIGS. 1–3, a cuff device or dynamic support for the lower extremity is shown, but it is understood that the principles of the invention are also applicable to other articulated body parts. There is shown in FIG. 1 a dynamic support 1 which includes an upper body part engaging cuff component 2 and a lower body part engaging cuff component 3. These cuff components comprise a fitting system and are respectively adapted to engage the body parts above and below the body articulation. A pair of arms 4 and 5 are respectively attached to and extend toward each other from the body part engaging cuff components 2 and 3. These arms 4 and 5 terminate in movable overlapping end regions 6 and 7 remote from the cuff components and are formed with aligned openings through which a single pivot pin 8 extends. A more complex slidable and pivotable orthotic joint can be used and additional arms can be located on the body parts. The pivot pin 8 has a head 9 and a section 10 secured in the opening in the end region 6 by a hexagonal shaped configuration complementary to a hexagonal shaped opening in end region 6. End region 7 pivots freely about pivot pin 8. Thus, pivot pin 8 forms a pivot axis which is substantially perpendicular to the arms 4 and 5 and which coincides with the predominant axis to which swinging of the upper and lower body parts are limited. The arms 4 and 5 may be of a slightly flexible material construction such as metal or plastic. The cuff components 2 and 3 are fixed at one end to the arms 4 and 5 by rivets 11 or the like. The cuff components are constructed of relatively soft yieldable material such as plastic or cloth to conform to the body part configuration. The opposite ends of the cuff components 2 and 3 are fixed to relatively stiff bars 12 and 13 by rivets 11 or the like.

A cable 14 is releasably and adjustably secured with a cable clamp bolt head 15 on arm 4, passes through a guide 16 on bar 12, passes through guide 17 on arm 4 and is directed in a groove around cam 18 of lever mechanism 19. The cable is
to the lower end of the cam 18 by a cable clamp then secured to the lower end of the cam 18 by a cable clamp bolt head (not shown) to provide a snug fit of the upper body part engaging cuff component and to prevent loosening of the cuff component from the snug fit position. The cam 18 is attached by bolts 20 or the like to lever 19 which is attached to end region 7 by bolts 20 or the like. The cable cam and lever can be constructed in various shapes and lengths to adjust the amount and rate of tightening of the cuff components and comprises a tightening system.

A cable 21 is secured under cable clamp bolt head 22 on bar 13, passes through guide 23 on arm 5 and is directed through guide 24 on lever 25 attached to end region 6 by bolt 25a or the like. The cable is then releasably and adjustably secured under a cable clamp bolt head 26 on arm 4 to provide a close fit of the lower cuff component. A lever 28 is adjustably attached to end region 7 by bolt 28a or the like and engages the cable 21 by a guide 29. The levers 25 and 28 of the tightening system can be adjusted such that the cuff component 3 is tightened away from the snug fit when the first body part is moved away from a predetermined position relative to the articulated second body part. In this instance tightening occurs in both flexion and extension of the thigh relative to the leg from the resting position.

In use, the dynamic support is placed on the wearer's body part by situating the upper and lower arms 4 and 5 in the region of the knee or other body articulation. The cuff components 2 and 3 are wrapped around the body parts and the cables 14 and 21 are adjustably secured under the appropriate cable clamp bolt heads 15 and 26. The dynamic support should fit snugly in the resting position for the articulation. The tightening system cable, lever and cam assembly is arranged and adjusted to tighten the cuff components when the body parts move in the direction of flexion and extension. However, numerous prophylactic and therapeutic conditions can be accommodated by various combinations and arrangements of the cables, levers and cams. One or both cuff components can be appropriately connected to the end regions to tighten in flexion or extension only or each in both directions from a predetermined position. One cuff device or dynamic support may serve to immobilize one arm and a tibia to prevent or restrain sliding or anterior and posterior movement of the tibia relative to the femur by arranging the system to dynamically tighten on the body parts in both flexion and extension. As another example, the dynamic support can serve to protect the knee from lateral bending and rotation by tightening both cuffs in extension of the extremity. Further, the tightening system can be arranged to first tighten the lower cuff component then the upper cuff component during the toe off and swing through phases of the wearer's gait to compress the body part to minimize stasis and improve fluid return.

Referring to FIG. 4, there is provided in accordance with another embodiment of the present invention, a dynamic support designated generally as 30. Except as hereinafter described, the dynamic support 30 is substantially identical to the dynamic support 1 and operates in the same manner for dynamically and temporarily tightening the cuff components on the body parts. For convenience, those features of the dynamic support which are identical to those of the dynamic support of FIGS. 1–3 are identified using the same numbers used in FIGS. 1–3. A pivot pin 8 is fixed in an opening in end region 7 as in the embodiment of FIGS. 1–3. A gear 31 is removably attached to the shaft of pivot pin 8 and rotates with pivot pin 8 relative to end region 7. A gear 32 is rotatably and removably attached to end region 7 by a bolt 33 of the like and has teeth that mesh with cooperating teeth on gear 31. Cable 14 passes from an upper body part engaging cuff component (not shown) and is secured in a groove in gear 32. Thus, hinging end regions 6 and 7 cause cable 14 to wind and unwind on gear 32 temporarily tightening and loosening the cuff component. Using interchangeable gears of various sizes, the rate and amount of tightening and loosening can be adjusted for the individual requirement. A lower body part engaging cuff component (not shown) may be held tightly in a static manner using a conventional strap and VELCRO brand strip or additional cables, gears, cams and levers may be utilized to provide a tightening system for the lower body part.

Referring to FIGS. 5–7 there is provided in accordance with still another embodiment of the present invention, a dynamic support designated generally as 40. Except as hereinafter described, the dynamic support 40 is substantially identical to the dynamic support 1 and operates in the same manner with a tightening system for dynamically and temporarily tightening the cuff components on the body parts. Those features of the dynamic support which are identical to those of the dynamic support of FIGS. 1–3 are identified using the same numbers used in FIGS. 1–3. Arms 4 and 5 and end regions 6 and 7 operate in the same manner as the arms and end regions in FIGS. 1–3. A cuff component 42 is fixed at one end to the arm 4 by rivets 43 or the like. The cuff component 42 passes around the body part (not shown), passes through a loop 44 and is adjustably and releasably fixed to itself by a VELCRO brand strip 45 or the like. The loop 44 is attached to a cable 46 which passes through guides 47 and 48 on arm 4 and is then directed around guide members 49 press fit in two of a series of holes 50 forming a cam plate in eand region 7 and is releasably secured by a press fit hook 51 in one of the holes in end region 7 or a hole in pivot pin 8. Thus, hinging end regions 6 and 7 causes the cable 46 to tighten the cuff component 42 in a direction generally transverse to the long axis of the body part when the arms are pivoted from the resting position. By guiding the cable around guide members selectively placed in holes in the end region, the resting position and rate and amount of temporary tightening and loosening can be adjusted for the individual requirement. End region 7 includes a slot 52 to slidably engage a screw 53 attached in one of a series of threaded holes 54 in end region 6 to provide a stop to limit the extent of movement of hinging end regions 6 and 7. A cuff component complementary to cuff component 42 may be fixed to end region 5 or to an arm located on the opposite side of the body part and connected by an arm to dynamic support 40.

To increase the amount of tightening by cuff component 42, an arrangement such as shown in FIG. 8 can be used. Cable 46 is replaced by cable segments 46a, 46b. Cable segment 46a connects loop 44 at one end, passes around a stationary guide 60, passes around a movable guide 62 and connects to stationary peg 64 at the other end. Guide 60 and peg 64 are mounted to arm 4 while movable guide 62 is secured to the free end of cable 62. Thus, movement of cable segment 46b one unit length pulls loop 44 two unit lengths. Other methods for increasing or decreasing the mechanical advantage of the embodiment of FIGS. 5–7 can be used as well.

Referring to FIG. 9 there is provided in accordance with still another embodiment of the present invention, a dynamic support designated generally as 70. Except as hereinafter described, dynamic support 70 is substantially identical to the dynamic support 1 and operates in the same manner with a tightening system for dynamically and momentarily tightening the cuff components on the body parts. Those features of the dynamic support which are identical to those of the dynamic support of FIGS. 1-3 are identified using the same numbers used in FIGS. 1-3. Arms 4 and 5 and end regions 6 and 7 operate in the same manner as those shown in FIGS. 1-3. A cuff component 72 consisting of a plurality of straps 73 and 74 is fixed at one end to the arm 4 by rivets 75 or the like. The straps 73 pass around the trunk or another body part, pass through loop 76 and are adjustably and releasably fixed to themselves by a Velcro ® strip 77 or the like. The straps 74 pass around the body part, pass through loop 78 and are adjustably and releasably fixed to themselves by a VELCRO brand strip or the like. The loop 76 is attached to cable 79 which passes through guides 80 and 81 on arm 4 and is then directed around guide member 82 press fit in one of a series of holes 83 formed in a cam plate in end region 7 and is releasably secured by press fit hook 84 in one of the holes in end region 7 or a hole in pivot pin 8. The loop 78 is attached to cable 85 which passes through guides 86 and 87 and is then directed around guide member 88 press fit in one of a series of holes 83 or a hole in pivot pin 8. Thus, hinging end regions 6 and 7 cause the cables 79 and 85 to tighten cuff component 72 in a direction generally transverse to the long axis of the body part when the arms are pivoted from the resting position. Depending on the location of guide members 82 and 88 in end region 7, the amount of tightening of cable 79 may be made different from the amount of tightening of cable 85. This differential amount of tightening allows for different support characteristics of straps 73 and 74 of cuff 72 and can be adapted to the needs of an individual patient. Dynamic support 70 of FIG. 9 is shown in a configuration where the straps 74 of cuff 72 tighten more than the straps 73 of cuff 72 due to the greater amount of tightening of cable 85 passing around guide member 88 which is located more radially outward and downward from pivot pin 8 than guide member 82 is located.

Cuff component 89 is fixed on one end to the arm 5 by rivets 90 or the like. The cuff component 89 passes around the limb or other body part, passes through loop 91 and is adjustably and releasably fixed to itself by a VELCRO brand strip 92 or the like. The loop 91 is attached to a cable 93 which passes through guides 94 and 95 on arm 5 and is then directed around a guide member 96 press fit in one of a series of holes 83 formed in the cam plate in end region 7 and is releasably secured by press fit hook 97 in a hole 98 in arm 4. Thus, hinging end regions 6 and 7 cause the cable 93 to tighten cuff component 89 in a direction generally transverse to the long axis of the body part when the arms are pivoted from the resting position. Dynamic support 70 may be accordingly provided on the opposite side of the body parts and integrated with cuff components 72 and 89.

By guiding the cable around guide members selectively placed in holes in the end region, the normal position and rate and amount of tightening and loosening can be adjusted to the individual requirement.

Referring to FIG. 10, there is provided in accordance with still another embodiment of the present invention, a dynamic support designated as 100. Except as hereinafter described, dynamic support 100 is substantially identical to the dynamic support 1 and operates in the same manner for dynamically and momentarily tightening the cuff components on the body parts. The features of the dynamic support of FIGS. 1-3 are identified using the same numbers used in FIGS. 1-3. Arms 4 and 5 and end regions 6 and 7 operate in the same manner as those shown in FIGS. 1-3. Strap 103 is wrapped around the body part. A cuff component 104 consisting of a plurality of straps 105 is fixed at one end to the arm 4 by rivets 106 or the like. The straps 105 pass around the body part, pass through slotted bar 107 and are adjustably and releasably fixed to themselves by VELCRO brand strips 108 or the like. Slotted bar 107 may be constructed of semi-rigid material such as plastic or the like and is rotatably fixed to arm 4 near the end region 6 by a pin 109 or the like. Cable 111 is secured under cable clamps bolt head 110 on bar 107, and is directed through guide 112, through guide 113 on arm 4 and is then directed around guide member 114 press fit in one of a series of holes 115 forming a cam plate in end region 7 and is releasably secured by press fit hook 116 in one of the holes in end region 7 or a hole in pivot pin 8. Thus, hinging end regions 6 and 7 cause the cable 111 to tighten cuff component 104 generally transverse to the long axis of the body part when the arms are pivoted from the resting position. By guiding the cable around guide members selectively placed in holes in the end region, the resting position and rate and amount of tightening and loosening can be adjusted to the individual requirement.

In the resting position, the upper straps 108 of cuff component 104 are fixed to the body part more loosely than the lower straps of cuff component 114. The semi-rigid nature of the slotted bar 107 allows it to progressively tighten cuff 104 beginning with the lower part of the body part and extending upwards until the last strap of cuff 104 is tightened. As each strap becomes tight due to the action of cable 111, slotted bar 107 flexes and limits the tightness at that strap but allows for the progressive tightening of straps above it.

Details have been disclosed to illustrate the invention in a preferred embodiment of which adaptation and modification within the spirit and scope of the invention will occur to those skilled in the art. The scope of the invention is limited only by the following claims.

What is claimed is:

1. A dynamic support for first and second body parts which are articulated to each other comprising cuff components adapted to snugly engage the first and second body parts when the first and second body parts are in a resting position, the cuff components engaging the first and second body parts at locations spaced from the body area where the body parts are articulated, arms attached to and extending from each of the cuff components and terminating in end regions, said end regions being movably attached to each other at a point adjacent to the area where the body parts are articulated, a tightening system attached to at least one of the cuff components and at least one end region; said dynamic support being characterized in that the tightening system includes members responsive to a predetermined relative movement between the body parts in at least one direction away from the resting position for increasing the tightness with which at least one of the cuff components engages at least one of the body parts.

2. A dynamic support according to claim 1 wherein the body parts are movable in opposite directions from the resting position and said tightening system temporarily increases the tightness with which at least one of the cuff components engages at least one of the body parts when at least one of the body parts moves in either one of the opposite directions.

3. A dynamic support according to claim 1 wherein the cuff components comprise members for varying the tightness with which the cuff components engage the body parts when in the resting position.

4. A dynamic support according to claim 1 wherein the tightness increasing system temporarily increases the tightness with which at least one of the cuff components engages at least one of the body parts.

5. A dynamic support according to claim 1 wherein the arms comprise members for pivoting one arm relative to the other arm.

6. A dynamic support according to claim 1 wherein said tightening system comprises a cable and lever assembly operatively coupling at least one of the cuff components with the arms attached thereto.

7. A dynamic support according to claim 6 wherein said tightening system further comprises a cam mechanism.

8. A dynamic support according to claim 1 wherein said tightening system comprises an adjustable cam and cable assembly operatively coupling the cuff components with the arms.

9. A dynamic support according to claim 8 wherein the cam and cable assembly comprises members for operatively coupling the cam and cable assembly to end regions.

10. A dynamic support according to claim 8 wherein the cam and cable assembly comprises members for adjusting the relative position of the arms when the first and second body parts are in their resting positions.

11. A dynamic support according to claim 8 wherein the cam and cable assembly further comprises a plate with multiple guide member holes.

12. A dynamic support according to claim 11 wherein the guide member holes releasably receive guide member pins.

13. A dynamic support according to claim 8 wherein the cam and cable assembly comprises members for limiting the extent of movement of the arms.

14. A dynamic support according to claim 13 wherein the members for limiting the extent of movement of the arms comprises stop members on the arms.

15. A dynamic support according to claim 14 wherein the stop members comprise a slot in one arm and a screw member in the other arm.

16. A dynamic support according to claim 1 wherein said tightening system comprises movable means.

17. A dynamic support according to claim 16 wherein said tightening system comprises a cable and gear assembly operatively coupling at least one of the cuff components with the arms attached thereto.

18. A dynamic support according to claim 16 wherein said tightening system comprises members responsive to a predetermined movement from a resting position in more than one direction of one body part relative to the other body part.

19. A dynamic support according to claim 16 wherein said tightening system responsive to a predetermined relative movement is responsive to a predetermined flexion and extension of one body part relative to the other body part.

20. A dynamic support according to claim 16 wherein said tightening system responsive to a predetermined relative movement is responsive to a predetermined flexion of one body part relative to the other body part.

21. A dynamic support according to claim 16 wherein said tightening system responsive to a predetermined relative movement is responsive to a predetermined extension of one body part relative to the other body part.

22. A dynamic support according to claim 16 wherein said tightening system responsive to a predetermined relative movement is responsive to a predetermined sliding movement of one body part relative to the other body part.

23. A dynamic support according to claim 16 wherein said tightening system responsive to a predetermined relative movement is responsive to rotation of one body part relative to the other body part.

24. A dynamic support according to claim 16 wherein said tightening system responsive to a predetermined relative movement is responsive to a predetermined movement of the body leg relative to the body thigh.

25. A dynamic support according to claim 16 wherein said tightness increasing system temporarily increase the tightness of the fit between the cuff components and the body leg.

26. A dynamic support according to claim 16 wherein said tightness increasing system temporarily increase the tightness of the fit between the cuff component and the body thigh.

27. A dynamic support according to claim 16 wherein said tightness increasing system comprises a means for increasing the mechanical advantage of the movable means.

28. A dynamic support according to claim 16 wherein said tightness increasing system increases the tightness of the fit in a direction generally transverse to a long axis of the body part.

29. A dynamic support according to claim 16 wherein said tightness increasing system adjusts the amount of tightening of at least one of the cuff components.

30. A dynamic support for body parts articulated to each other comprising a fitting system for providing a close fit between the dynamic support and the body parts; arms attached to and extending from the fitting system and terminating in end regions movably attached to each other remote from the fitting system: a tightening system attached to the fitting system and the arms responsive to a predetermined movement of one body part in more than one predetermined direction away from a predetermined position relative to the other body part for temporarily increasing the tightness of the fitting system on at least one of the body parts; members for varying the rate of tightening of the fitting system; and members for preventing a loosening of the fitting system.

31. A dynamic support according to claim 30 wherein the tightening system comprises an adjustable cam assembly.

32. A dynamic support according to claim 30 wherein the tightening system comprises members for adjusting the amount of tightening of the fitting system.

33. A dynamic support for first and second body parts of a body articulated to each other by a joint permitting generally pivotal movements of the parts about a pivot axis with respect to each other from a resting position in which the parts are in an angular inclination relative to each other to a temporary position in which the parts are in a different angular inclination relative to each other, the support compromising cuff members engaging the first and second body parts in their resting position with a predetermined tightness, the cuff members being constructed so as to have a component on each side and spaced from the joint when applied to the first and second body parts of the patient, arms connected with the cuff members and having end regions, said arms in substantial alignment with the longitudinal axes or the body parts, and members pivotally securing the end regions of the arms to each other substantially coaxially with the pivot axis: a tightening system attached to the cuff members and the end regions of the arms for increasing the tightness with which the cuff members engages at least one of the body parts when they are moved far away from the resting position towards the temporary position.

34. A dynamic support according to claim 33 including members for varying the rate at which the tightening system increases the tightness with which the cuff members engages at least one of the body parts.

35. A dynamic support according to claim 34 wherein the members for varying the rate includes an adjustable cam assembly.

36. A dynamic support for first and second body parts which are articulated to each other comprising cuff components adapted to snugly engage the first and second body parts when the first and second body parts are in a resting position;

the cuff components engaging the first and second body parts at locations spaced from the body area where the parts are articulated;

arms attached to and extending from each of the cuff components and terminating in end regions; said end regions being movably attached to each other at a point adjacent the area where the body parts are articulated remote from the cuff components;

a tightening system attached to at least one of the cuff components and at least one arm; and the tightening system including members responsive to a predetermined relative movement between the body parts in extension from the resting position for increasing the tightness with which at least one of the cuff components engages at least one of the body parts.

37. A dynamic support for first and second body parts which are articulated to each other comprising cuff components adapted to snugly engage the first and second body parts when the first and second body parts are in a resting position, the cuff components engaging the first and second body parts at locations spaced from the body area where the body parts are articulated, arms attached to and extending from each of the cuff components and terminating in end regions, said end regions being movably attached to each other at a point adjacent to the area where the body parts are articulated, a tightening system attached to at least one of the cuff components and at least one end region; said dynamic support being characterized in that the tightening system includes members responsive to a predetermined relative movement between the body parts in at least one direction away from the resting position for differentially increasing the tightness with which at least one of the cuff components engages at least one of the body parts.

38. A dynamic support according to claim 37 wherein said tightening system includes members responsive to a predetermined relative movement between the body parts for progressively increasing the tightness with which at least one of the cuff components engage at least one of the body parts.

* * * * *